United States Patent [19]
Grant et al.

[11] Patent Number: 5,791,944
[45] Date of Patent: Aug. 11, 1998

[54] ELECTRODE CONNECTOR

[75] Inventors: John L. Grant, Sherborn; Herbert J. McEvoy, North Attleboro, both of Mass.

[73] Assignee: Cambridge Heart, Inc., Bedford, Mass.

[21] Appl. No.: 724,885

[22] Filed: Oct. 3, 1996

[51] Int. Cl.$^6$ ............................................. H01R 4/48
[52] U.S. Cl. ............................................. 439/822
[58] Field of Search ........................... 439/909, 729, 439/822, 67, 493

[56] References Cited

U.S. PATENT DOCUMENTS

| | | | |
|---|---|---|---|
| 4,082,087 | 4/1978 | Howson | 128/2.06 E |
| 4,362,165 | 12/1982 | Carmon et al. | 128/640 |
| 4,365,634 | 12/1982 | Bare et al. | 128/640 |
| 4,448,199 | 5/1984 | Schmid | 128/639 |
| 4,550,961 | 11/1985 | Aicher et al. | 439/909 |
| 4,583,549 | 4/1986 | Manoli | 128/640 |
| 4,583,551 | 4/1986 | Pike | 128/640 |
| 4,763,660 | 8/1988 | Kroll et al. | 128/640 |
| 4,797,125 | 1/1989 | Malana | |
| 4,873,973 | 10/1989 | Hagen et al. | 439/909 |
| 4,951,672 | 8/1990 | Buchwald et al. | 128/653 SC |
| 4,955,381 | 9/1990 | Way et al. | 128/640 |
| 4,955,383 | 9/1990 | Faupel | 128/653 R |
| 5,184,620 | 2/1993 | Cudahy et al. | 128/639 |
| 5,224,479 | 7/1993 | Sekine | 128/644 |
| 5,259,387 | 11/1993 | dePinto | 128/696 |
| 5,265,617 | 11/1993 | Verrier et al. | 128/704 |
| 5,295,482 | 3/1994 | Clare et al. | 128/639 |
| 5,366,497 | 11/1994 | Ilvento et al. | 607/142 |
| 5,507,290 | 4/1996 | Kelly et al. | 128/640 |
| 5,520,683 | 5/1996 | Subramaniam et al. | 606/32 |

FOREIGN PATENT DOCUMENTS

WO 91/19531  12/1991  WIPO

Primary Examiner—Hien Vu
Assistant Examiner—Yong Kim
Attorney, Agent, or Firm—Fish & Richardson P.C.

[57] ABSTRACT

A connector that connects an electrode to a lead includes a connector housing. A conductive contact is positioned in the connector housing and has a tapered end, and a seating surface is positioned in the connector housing opposite the tapered end of the conductive contact. The seating surface and the tapered end are configured to positively retain an electrode when a connection hole of the electrode is positioned around the tapered end. The connector also includes a mechanism for pressing the seating surface against the tapered end of the conductive contact.

19 Claims, 9 Drawing Sheets

ELECTRODE CONNECTOR

This application claims priority from U.S. application Ser. No. 08/665,434, entitled "Electrode Connector" and filed Jun. 18, 1996.

BACKGROUND OF THE INVENTION

The invention relates to a connector for attaching an electrode to a lead.

Connectors are used often to attach an electrode to a lead. This attachment may be temporary. For example, many medical systems, such as electrocardiogram (ECG) systems, include connectors for attachment of electrodes to leads of the systems. The electrodes typically are designed to be discarded after a single use. For this reason, the connectors should provide for uncomplicated attachment and removal of the electrodes.

SUMMARY OF THE INVENTION

The invention provides an improved connector for attaching an electrode to a lead. The connector includes at least one conductive contact having a tapered end. The contact is positioned on one side of the path along which an electrode is inserted into the connector. A seating surface is positioned opposite the contact on the other side of the electrode insertion path. The seating surface may be a deformable surface such as a surface of a piece of foam. The seating surface also may be a rigid surface having a cutout or indentation in a position corresponding to the contact.

The tapered end of the contact extends through a connection hole in an electrode when the electrode is attached to the connector. The contact is shaped to conform to the shape of the hole and is sized so that the largest cross section of the taper is larger than the connection hole and the smallest cross section of the taper is smaller than the connection hole. This arrangement centers the connection hole about the contact to ensure a good electrical conductive path between the contact and the electrode.

The electrical connection is further improved by having the seating surface press the electrode against the contact. The portion of the electrode surrounding the connection hole may be made from a flexible material such as polyester film (e.g., Mylar). In this case, pressure applied to the electrode by the surface conforms the electrode material to the shape of the contact and increases the amount of surface area of the electrode that touches the contact.

The contact-and-hole arrangement positively attaches the electrode to the connector. This may be contrasted to prior art arrangements in which leaf springs or similar means used frictional forces to hold the electrode in the connector. Unlike the contact-and-hole arrangement, the springs of the prior art arrangement were subject to wear due to abrasion. This wear necessitated replacement of a connector after a relatively small (e.g., 50) number of uses to ensure that the connector would provide a good electrical connection between an electrode and a lead.

In one aspect, generally, the invention features a connector for connecting an electrode to a lead. The connector includes a connector housing, a conductive contact positioned in the connector housing and having a tapered end, and a seating surface positioned in the connector housing opposite the tapered end of the conductive contact. The seating surface and the tapered end of the conductive contact are configured to positively retain an electrode when a connection hole of the electrode is positioned around the tapered end of the conductive contact. The connector also includes a mechanism for pressing the seating surface against the tapered end of the conductive contact.

Embodiments of the invention may include one or more of the following features. A cross section of the conductive contact about an axis along which the contact tapers may be sized at a first position to be smaller than a connection hole in an electrode to be inserted into the connector. The cross section also may be sized at a second position to be larger than a connection hole in the electrode. This ensures that the electrode will fit snugly against the contact regardless of manufacturing variations in the size of the connection hole.

The connector may include more than one contact. For example, a connector configured for use with a multi-segment electrode having four segments may include four contacts. Each contact may taper to a point, or may include a flat or rounded end. Similarly, the taper may be a continuous taper or a step taper. For example, a contact could include a cylindrical bottom on which one or more smaller diameter cylinders are stacked. The contact also may include nonconductive portions. The contact may be circular, or may have square, triangular or other cross sections.

The connector may include an insertion path along which an electrode is inserted into the connector housing. The conductive contact may taper along an axis that is generally perpendicular to the insertion path. In addition, the contact may be positioned on a first side of the insertion path while the seating surface is positioned on an opposite side of the insertion path.

The seating surface may be a deformable surface and the mechanism may apply pressure sufficient to deform the deformable surface. The deformable surface may be the surface of a piece of foam or similar material.

The connector housing may include a top portion to which the seating surface is attached and a bottom portion to which the conductive contact is attached. The top portion may be connected to the bottom portion by a hinge, and the connector may include a spring configured to bias the seating surface against the contact.

The spring and the seating surface may be configured to provide pressure sufficient to deform an electrode in a region surrounding the conductive contact. By deforming the electrode, the spring and seating surface cause an increased surface area of the electrode to touch the surface of the contact. This improves the conductive path from the contact to the electrode.

An electrode for use with the connector may include a connection hole positioned around the tapered end of the conductive contact. The electrode also may include a center segment and segments positioned around the center segment, with connection holes corresponding to each segment. The connector may include conductive contacts corresponding to each connection hole in the electrode. The mechanism and the seating surface may be configured to provide pressure sufficient to deform the electrode in regions surrounding the connection holes.

The connector may be included in an electrocardiogram (ECG) system. The ECG system also may include an electrode connected to the connector and configured for attachment to a patient's skin to detect electrical signals produced by the patient's heart, a processor, and a lead connected between the connector and the processor to deliver electrical signals detected by the electrode from the connector to the processor. The processor may be configured to process the electrical signals to detect alternans.

In another aspect, generally, the invention features an electrode configured for use with a connector that includes a connector housing, a conductive contact positioned in the connector housing and having a tapered end, a seating surface positioned in the connector housing opposite the tapered end of the conductive contact, and a mechanism for pressing the seating surface against the tapered end of the conductive contact. The electrode includes a basepad and a connection hole formed in the basepad. The connection hole is larger than a first portion of the tapered end of the conductive contact and smaller than a second portion thereof. The electrode also includes a terminal formed on the basepad and a conductive path formed on the basepad from the terminal to a region surrounding the connection hole.

The basepad may be configured to be deformed in a region surrounding the connection hole by pressure applied by the seating surface and the mechanism. For example, the basepad may be made from a thin polyester film.

The electrode also may include multiple connection holes formed in the basepad. Each of the connection holes is larger than a first portion of the tapered end of the contact and smaller than a second portion thereof. Multiple terminals may be formed on the basepad, with conductive paths formed on the basepad from each of the terminals to a region surrounding a corresponding connection hole. The terminals may include a center segment and multiple segments surrounding the center segment.

Other features and advantages of the invention will become apparent from the following description of the preferred embodiment, including the drawings, and from the claims.

DESCRIPTION OF THE PREFERRED EMBODIMENT

Figure 1:
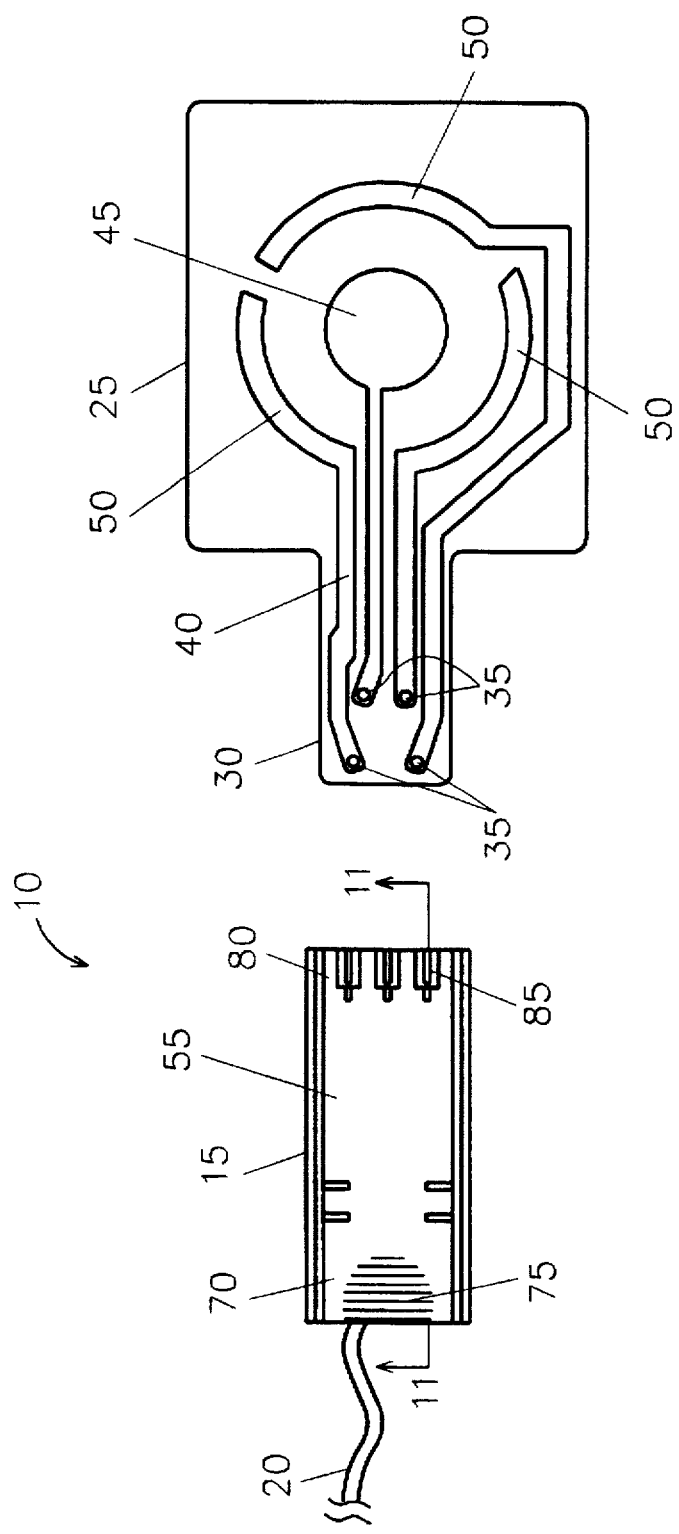
FIG. 1 is a top view of a connector assembly and an electrode.
Figure 2:
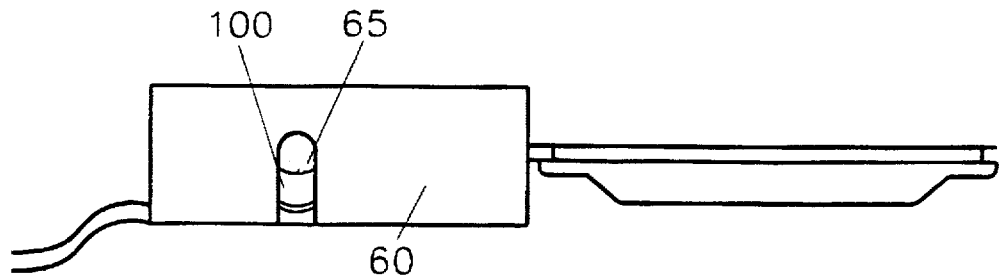
FIG. 2 is a side view of a connector of the assembly of FIG. 1 in a closed configuration with an electrode attached.

Referring to FIG. 1, a connector assembly 10 includes a connector 15 attached to an end of a lead 20. A multi-segment electrode 25 is configured for use with the connector 15 and includes a connection tail 30. Four connection holes 35 are positioned in a square pattern on the connection tail 30. Each hole 35 passes through an extension 40 of a segment of the electrode 25. The electrode includes a center segment 45 and a trio of annular segments 50 that together surround the center segment.

Referring also to FIGS. 2–8, the connector 15 includes a connector top 55 and a connector bottom 60. The connector top 55 includes a pair of hinges 65 that attach the connector top to the connector bottom 60 in a rotatable manner. The hinges are positioned on opposite sides of the connector top and are offset from a center point of the connector top toward the rear 70 of the connector top. As discussed below, the connector may be opened by depressing the rear of the connector top to cause the connector top to rotate about an axis defined by the hinges 65 (see FIG. 5). The rear of the connector top includes a series of raised ridges 75 that together define a finger grip for use in depressing the rear of the connector top.

The front 80 of connector top 70 includes three flexible guide ribs 85. The guide ribs are attached to the bottom of the connector top at the front of the connector top on one end and are free on the other end. The guide ribs extend beneath the connector top from the front of the connector top toward the rear of the connector top. The guide ribs serve to guide the tail 30 of the electrode 25 into the connector 15. Since the guide ribs are flexible, they also serve to relieve stress on the tail 30 during use. In addition, the guide ribs provide a flexible curved surface that permits the connector to be twisted slightly relative to the electrode without pulling the electrode away from the patient to which the electrode is attached.

A layer of compressible foam 90 is attached to the bottom of the connector top. The foam extends from the free end of the ribs 85 to the hinges 65. As discussed below, the foam provides a deformable surface that accepts contacts 95 of the connector bottom 60.

Referring also to FIGS. 9–12B, the connector bottom 60 includes a pair of openings 100 that are sized to accept the hinges 65 of the connector top 55. An opening 105 sized to accept the lead 20 is positioned at the rear 110 of the connector bottom 60. The rear of the connector bottom also includes a ledge 115 that is positioned to receive the rear edge 70 of the connector top 55 when the connector top 55 is depressed. Like the connector top, the connector bottom includes three flexible guide ribs 85. The ribs extend from the top front 120 of the connector bottom.

Four contact receptacles 125 are positioned within the connector bottom 60 toward the front 120 of the connector bottom. Each contact receptacle is sized and shaped to receive a contact 95 and to hold the contact in place through an interference relationship. When the connector 15 is assembled, the receptacles 125 are surrounded by a layer of foam 130.

Each receptacle includes a pair of slots 135 through which a wire 140 of the lead 20 may be inserted. When a contact is positioned in a receptacle, the contact presses against the wire 140 to form a conductive path from the contact to the wire.

The connector bottom also includes a lead guide 145 and a pair of strain relief posts 150. The guide and posts are used in positioning the lead 20 and relieving stress on the wires 140. A post 155 and a pair of grooves 160 operate in conjunction with the lead guide 145 to position a spring 165 within the connector 15. The spring 165 biases the connector 15 in a closed position. An arm of the spring 165 presses against the lead 20 to provide additional strain relief.

The connector top 55 and the connector bottom 60 are made from molded plastic. They also may be made from other suitable materials.

Figure 13:
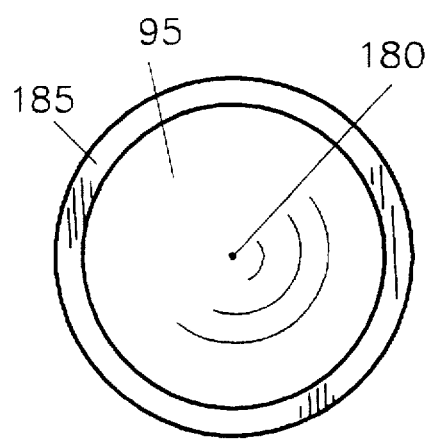
FIGS. 13 and 14 are side and top views of a contact of the connector of FIG. 2.
Figure 14:
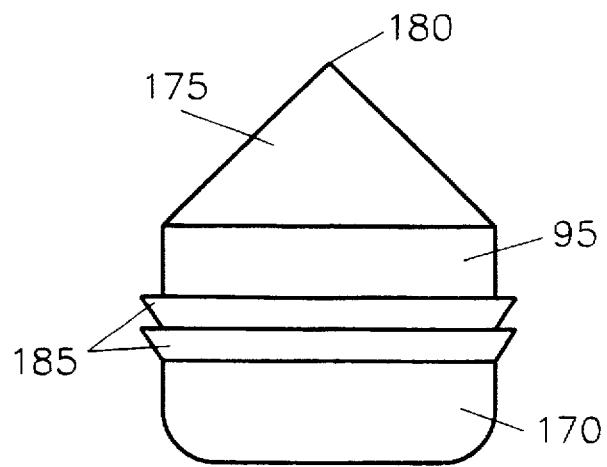
Figure 12A:
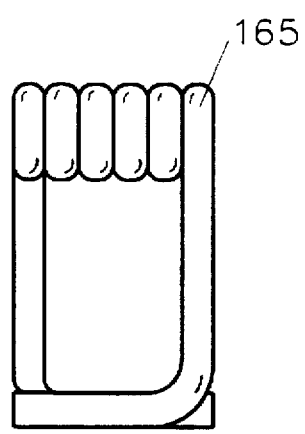
FIGS. 12A and 12B are top and side views of a spring of the connector of FIG. 2.
Figure 12B:
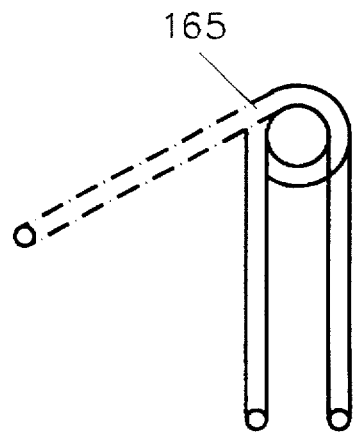

Referring to FIGS. 13 and 14, the contacts 95 have a generally circular shape. Each contact includes a cylindrical bottom portion 170. A top portion 175 of the contact tapers from the bottom portion to a point 180. The top portion 175 also could taper to a flat or rounded surface. A pair of deformable ridges 185 encircle the bottom portion 170. These ridges improve the interference fit of the contact within the receptacle 125.

Figure 15:
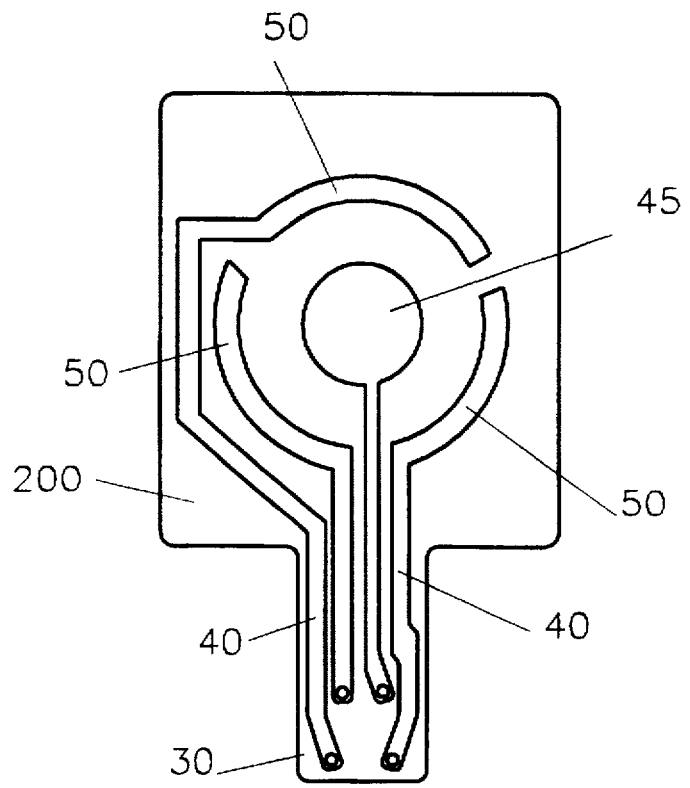
FIGS. 15 and 16 are top and side views of an electrode.
Figure 16:
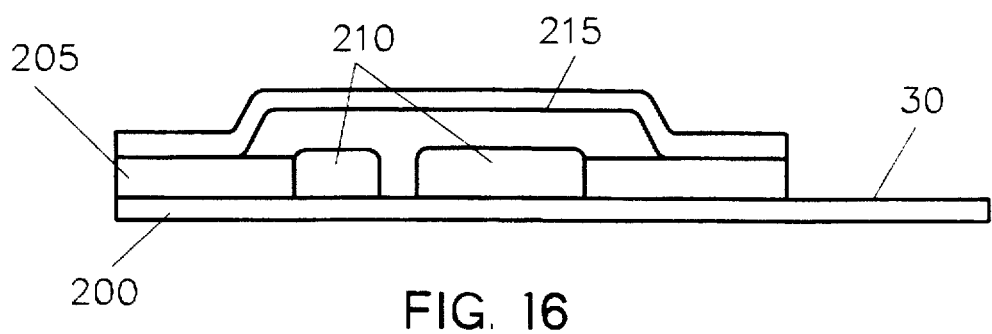

Referring to FIGS. 15 and 16, the multi-segment electrode 25 is formed on a basepad 200. The basepad may be made from an insulating, flexible film (e.g., polyester film). The connection tail 30 is a portion of the basepad, and the holes 35 pass through the basepad.

The extensions 40 and the segments 45, 50 are formed by printing with silver-chloride ink on the basepad 200. The silver-chloride ink is printed on the bottom of the basepad 200. With the exception of portions adjacent to the holes 35, a layer of insulating material covers the silver-chloride ink that defines the extensions 40.

A layer of plastic flexible foam 205 covers the bottom of the basepad 200. An adhesive is positioned on the surface of the foam to hold the electrode to the skin of the patient. The foam also includes wells 210 that correspond to the segments 45, 50. The wells are filled with conductive gel that provides conductive paths from a patient's skin to the silver-chloride ink that defines the segments 45, 50. In storage and prior to use, a cover 215 is positioned over the foam 205.

Figure 17A:
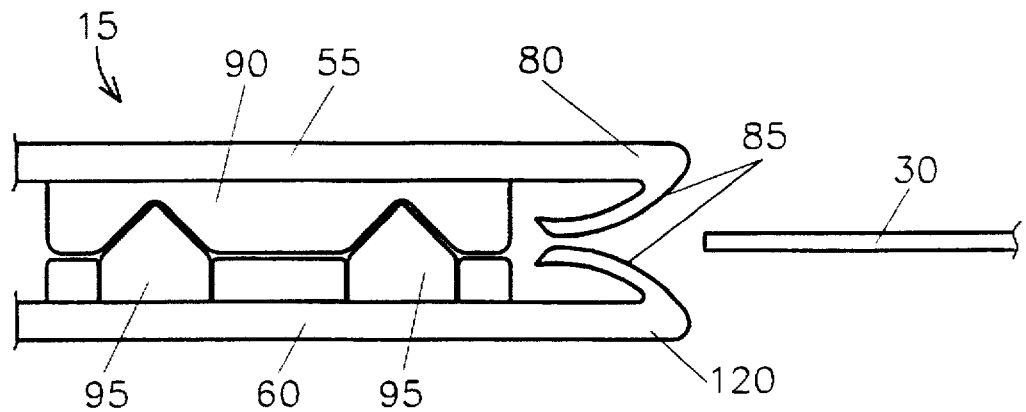
FIGS. 17A–17D are schematic illustrations of operation of the connector of FIG. 2.

FIGS. 17A–17D illustrate how the connection tail 30 of the electrode 25 is inserted into the connector 15. Initially, the connector 15 is in a closed position and the connection tail 30 is not attached to the connector (FIG. 17A). In this configuration, the layer of foam 90 on the bottom of the connector top 55 is deformed by the tapered top portions 175 of the contacts 95.

Figures 3, 4:
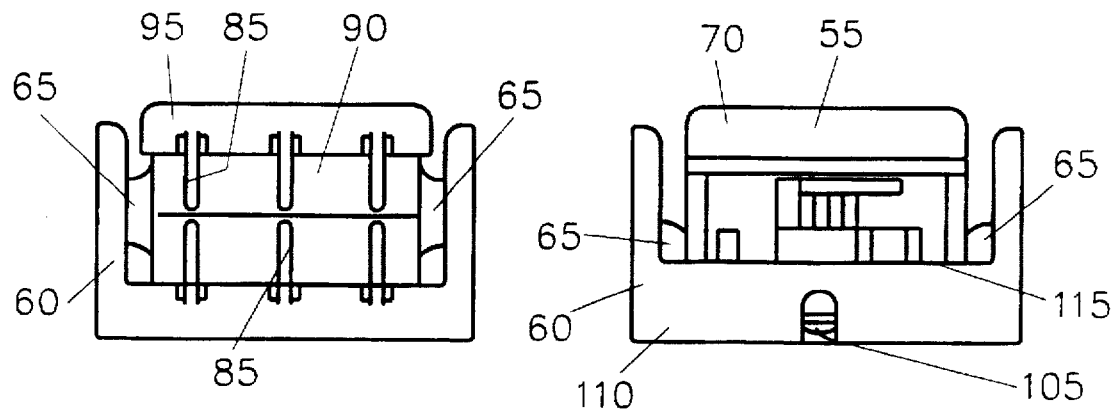
FIGS. 3 and 4 are front and rear views of the connector of FIG. 2 without an electrode attached.
Figure 5:
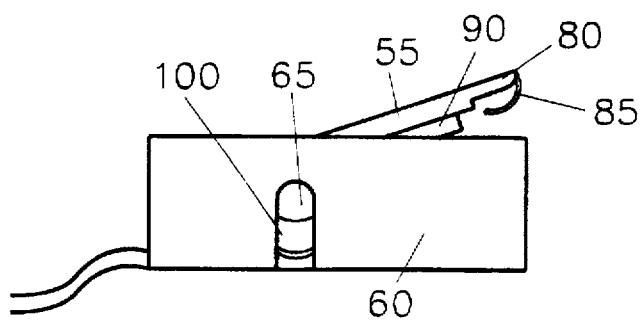
FIG. 5 is a side view of the connector of FIG. 2 in an open configuration.
Figure 6:
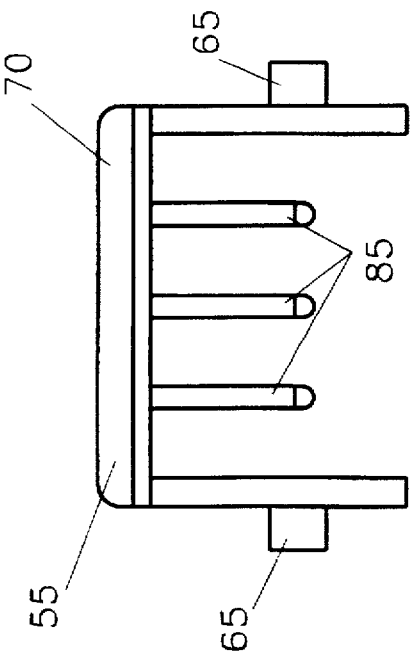
FIGS. 6-8 are top, side and end views of a top portion of the connector of FIG. 2.
Figure 8:
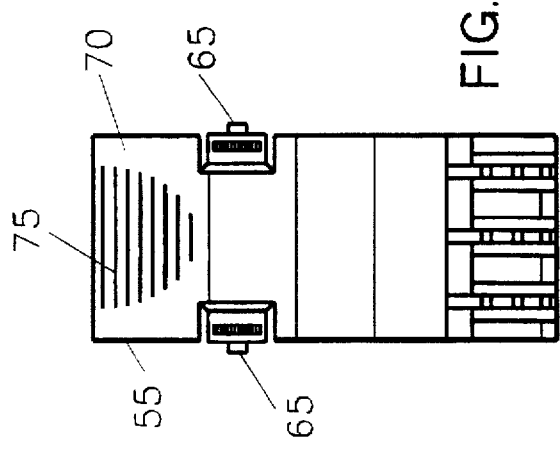
Figure 7:
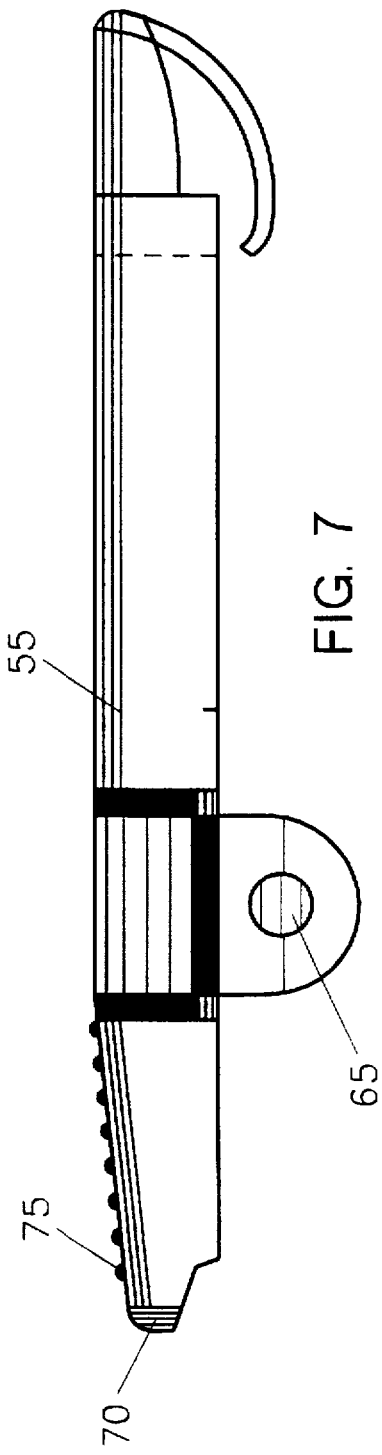
Figure 10:
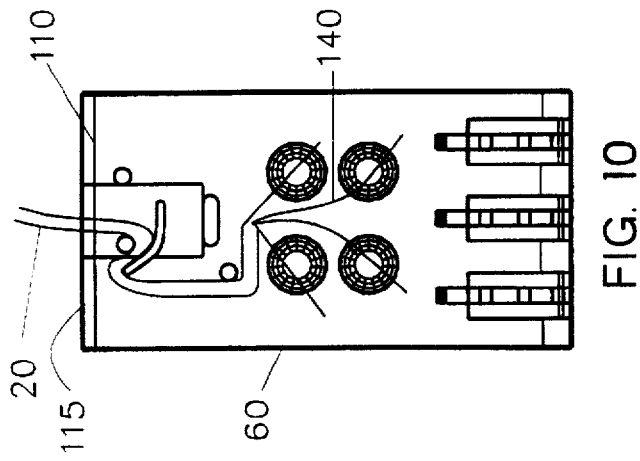
FIG. 10 is a top view of the bottom portion of the connector of FIG. 2 with a lead attached.
Figure 9:
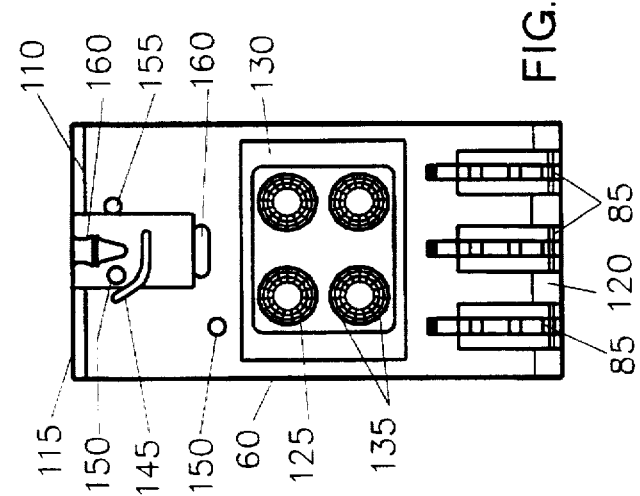
FIG. 9 is a top view of a bottom portion of the connector of FIG. 2 with no lead attached.
Figure 11:
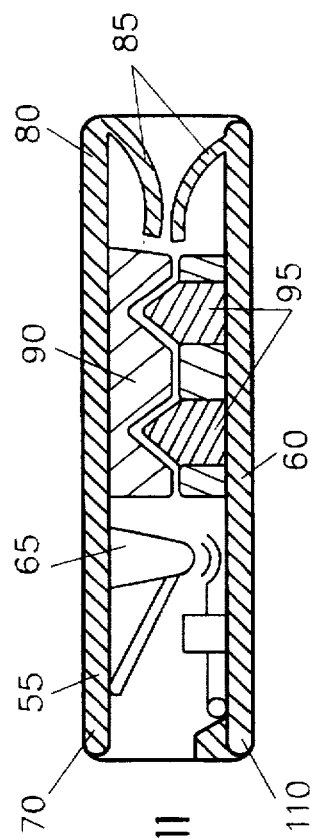
FIG. 11 is a sectional view of the connector of FIG. 1 taken along section 11—11 of FIG. 1.
Figure 17B:
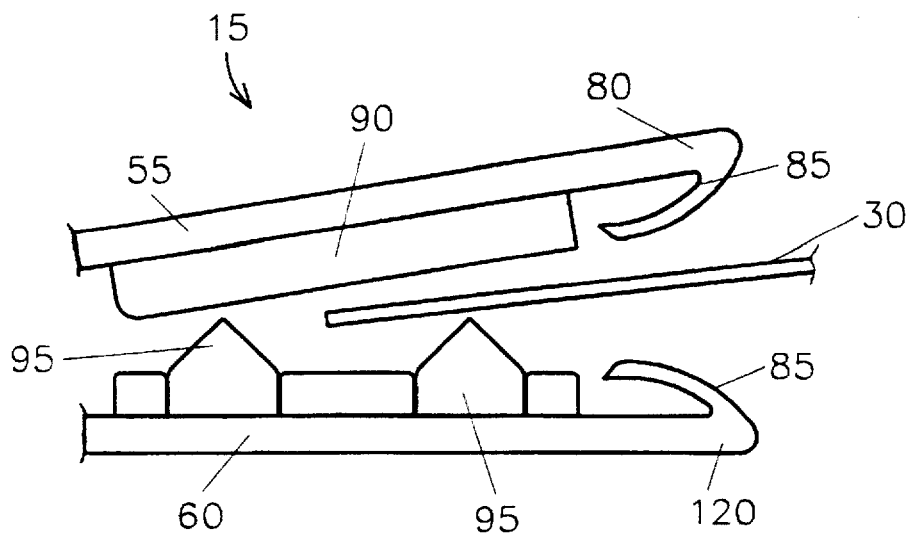
Figure 17C:
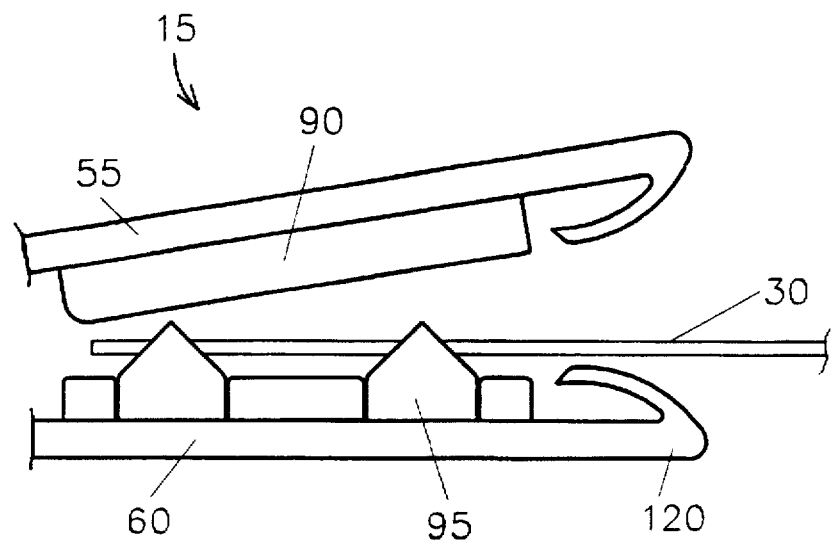

Next, the rear 70 (FIG. 1) of the connector top 55 is depressed to move the connector top away from the connector bottom 60 (FIGS. 3 and 17B). This permits insertion of the connection tail 30 between the contacts 95 and the foam 90. The connection tail is inserted until the holes 35 in the connection tail are aligned with the points 180 of the contacts (FIG. 17C).

Figure 17D:
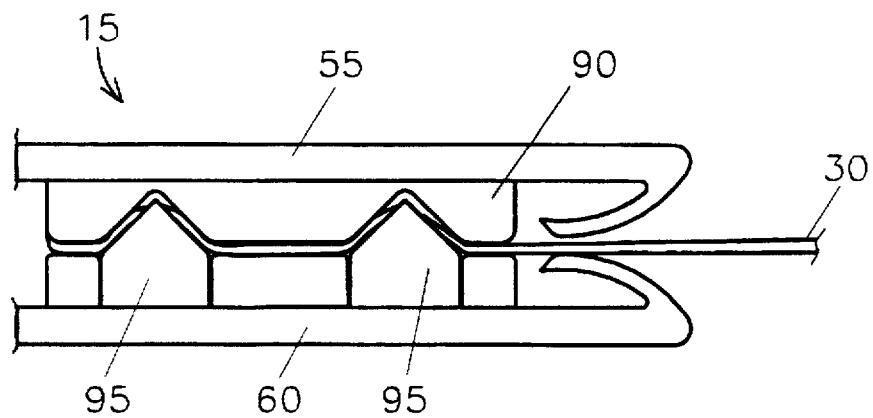

Finally, the connector top is released, which allows the spring 165 (FIG. 11) to move the connector top against the connector bottom (FIG. 17D). In this configuration, the foam 70 presses the connection tail against the tapered ends of the contacts. Pressure applied by the spring 165 through the foam 70 deforms the connection tail at the holes 35. This ensures that there will be a good conductive path between the contacts and the silver-chloride ink surrounding the holes 35.

Figure 18:
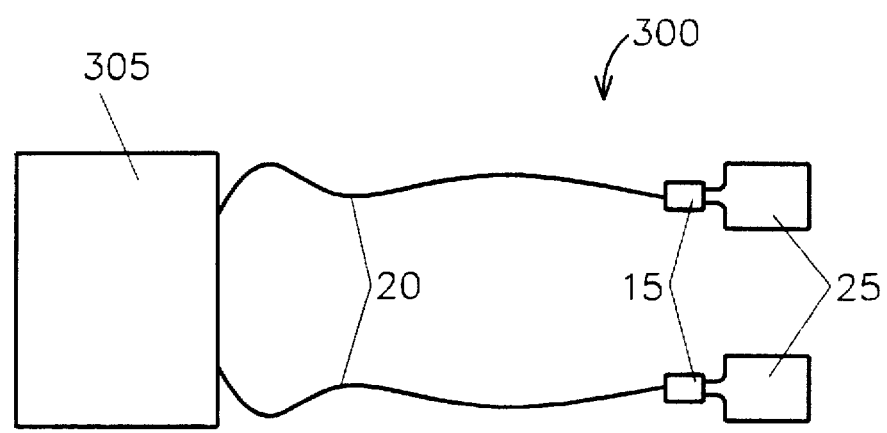
FIG. 18 is a block diagram of an electrocardiogram system.

Referring to FIG. 18, connector assemblies 10, leads 20, and electrodes 25 may be included in an electrocardiogram (ECG) system 300 that also includes a processor 305. The electrodes 25 are attached to a patient's skin and positioned to detect electrical signals produced by the patient's heart. The processor 305 may be configured to detect alternans, a subtle beat-to-beat change in the repeating pattern of an ECG waveform, which can be indicative of electrical instability of the heart and increased susceptibility to sudden cardiac death. ECG systems configured to detect alternans are discussed in U.S. application Ser. No. 08/379,375, filed Jan. 26, 1995 and entitled "Measuring and Assessing Cardiac Electrical Stability", and U.S. application Ser. No. 08/557,883, filed Nov. 14, 1995, and entitled "Using Related Signals to Reduce ECG Noise". Both of these applications are incorporated herein by reference.

Other embodiments are within the following claims. For example, the deformable surface could be replaced with a rigid surface having a cutout shaped to conform to the shape of the tapered end. Similarly, the electrode could be implemented using a standard electrode to which is attached an adapter having a connection hole. In this instance, the electrode and the adapter together would constitute an electrode within the claims.

What is claimed is:

1. A connector for connecting to a lead an electrode including a basepad, a connection hole formed in the basepad, a terminal formed on the basepad, and a conductive path formed on the basepad from the terminal to a region surrounding the connection hole, the connector comprising:

a connector housing, a conductive contact positioned in the connector housing and having a tapered end, a seating surface positioned in the connector housing opposite the tapered end of the conductive contact, the seating surface and the tapered end of the conductive contact being configured to positively retain an electrode when a connection hole of the electrode is positioned around the tapered end of the conductive contact; and a mechanism for pressing the seating surface against the tapered end of the conductive contact;

wherein a cross section of the conductive contact about an axis along which the contact tapers is sized at a first position to be smaller than a connection hole in an electrode to be inserted into the connector and is sized at a second position to be larger than a connection hole in an electrode to be inserted into the connector.

2. The connector of claim 1, further comprising at least one additional conductive contact having a tapered end.

3. The connector of claim 1, wherein the conductive contact tapers to a point.

4. The connector of claim 1, wherein the conductive contact is circular about an axis along which the conductive contact tapers.

5. The connector of claim 1, wherein the conductive contact tapers along an axis that is generally perpendicular to a path along which an electrode is inserted into the connector housing.

6. The connector of claim 5, wherein the conductive contact is positioned on a first side of the electrode insertion path and the seating surface is positioned on a second side of the electrode insertion path.

7. The connector of claim 1, wherein the seating surface comprises a deformable surface and the mechanism applies pressure sufficient to deform the deformable surface.

8. The connector of claim 1, wherein the connector housing includes a top portion to which the seating surface is attached and a bottom portion to which the conductive contact is attached.

9. The connector of claim 8, wherein the top portion is connected to the bottom portion by a hinge.

10. The connector of claim 9, wherein the mechanism comprises a spring configured to bias the seating surface against the conductive contact.

11. The connector of claim 1, wherein the mechanism and the seating surface are configured to provide pressure sufficient to deform an electrode in a region surrounding the conductive contact.

12. The connector of claim 1, further comprising an electrode, wherein a connection hole defined in the electrode is positioned around the tapered end of the conductive contact.

13. The connector of claim 12, wherein a cross section of the conductive contact about an axis along which the contact tapers is sized at a first position to be smaller than the connection hole in the electrode and at a second position to be larger than the connection hole in the electrode.

14. The connector of claim 12, wherein:
   the electrode comprises a center segment and segments positioned around the center segment,
   the electrode includes connection holes corresponding to each segment, and
   the connector includes conductive contacts corresponding to each connection hole in the electrode.

15. The connector of claim 12, wherein the mechanism and the seating surface are configured to provide pressure sufficient to deform the electrode in a region surrounding the connection hole.

16. An electrocardiogram system including the connector of claim 2.

17. The electrocardiogram system of claim 16, wherein the system further comprises:
   an electrode connected to the connector, the electrode being configured for attachment to a patient's skin to detect electrical signals produced by the patient's heart;
   a processor; and
   a lead connected between the connector and the processor to deliver electrical signals detected by the electrode from the connector to the processor.

18. The electrocardiogram system of claim 17, wherein the processor is configured to process the electrical signals to detect alternans.

19. A connector for connecting to a lead an electrode including a basepad, a connection hole formed in the basepad, a terminal formed on the basepad, and a conductive path formed on the basepad from the terminal to a region surrounding the connection hole, the connector comprising:
   a connector housing,
   a conductive contact positioned in the connector housing and having a tapered end,
   a seating surface positioned in the connector housing opposite the tapered end of the conductive contact, the seating surface and the tapered end of the conductive contact being configured to positively retain an electrode when a connection hole of the electrode is positioned around the tapered end of the conductive contact; and
   a mechanism for pressing the seating surface against the tapered end of the conductive contact;
   wherein the seating surface comprises a deformable surface, the mechanism applies pressure sufficient to deform the deformable surface, and the deformable surface comprises a surface of a piece of foam.

* * * * *

UNITED STATES PATENT AND TRADEMARK OFFICE
CERTIFICATE OF CORRECTION

PATENT NO. : 5,791,944

DATED : August 11, 1998

INVENTOR(S) : John L. Grant and Herbert J. McEvoy

It is certified that error appears in the above-identified patent and that said Letters Patent is hereby corrected as shown below:

Cover page, after line "[22] Filed:  Oct. 3, 1996", insert the following:

--Related U.S. Application Data

[63]  Continuation of Ser. No. 665,434, June 18, 1996, abandoned.--

Signed and Sealed this

Third Day of April, 2001

Attest:

NICHOLAS P. GODICI

*Attesting Officer*    *Acting Director of the United States Patent and Trademark Office*